United States Patent [19]

Kulkarni

[11] 4,181,983

[45] Jan. 8, 1980

[54] ASSIMILABLE HYDROPHILIC PROSTHESIS

[76] Inventor: R. K. Kulkarni, 4207 Briggs Chaney Rd., Beltsville, Md. 20705

[21] Appl. No.: 828,659

[22] Filed: Aug. 29, 1977

[51] Int. Cl.$^2$ .................... A61F 1/00; A61F 13/00
[52] U.S. Cl. ................................ 3/1; 3/1.9; 433/228; 128/156; 128/296; 128/325; 264/41; 264/48; 264/86; 264/87; 521/61; 521/88; 521/90; 521/98
[58] Field of Search .................. 32/1; 3/1, 1.9; 128/334 R, 335.5, 156, 296, 325; 521/61, 88, 90, 98; 264/48, 41, 86, 87

[56] References Cited

U.S. PATENT DOCUMENTS

| | | | |
|---|---|---|---|
| 3,463,158 | 8/1969 | Schmitt et al. | 3/1 |
| 3,566,871 | 3/1971 | Richter et al. | 128/296 |
| 3,797,499 | 3/1974 | Schneider | 128/334 R |
| 3,867,190 | 2/1975 | Schmitt et al. | 128/335.5 |
| 3,875,937 | 4/1975 | Schmitt et al. | 128/156 |
| 3,902,497 | 9/1975 | Casey | 128/296 |
| 3,942,532 | 3/1976 | Hunter et al. | 128/335.5 |
| 3,977,406 | 8/1976 | Roth | 128/296 |
| 3,978,855 | 9/1976 | McRae et al. | 128/156 |

OTHER PUBLICATIONS

Kulkarni, R. K., et al., J. Biomed. Mater. Res., vol. 5, pp. 169-181 (1971).
Cutright, D. E., et al., Oral. Surg., vol. 32, pp. 165-173 (1971).

*Primary Examiner*—Benjamin R. Padgett
*Assistant Examiner*—T. S. Gron
*Attorney, Agent, or Firm*—Frank E. Robbins

[57] ABSTRACT

A porous, hydrophilic, assimilable prosthesis is formed by the removal of solvent, without substantial dimensional change, from a solution of (a), an assimilable polymer composed primarily of polymerized units of an alpha or beta hydroxy carboxylic acid, preferably but not necessarily those having 1 to 4 carbon atoms, and (b), a small amount of a physiologically acceptable wetting agent that is sufficient to impart hydrophilicity to the prosthesis. The preferred assimilable polymer is a polylactic acid. The preferred process for making the prosthesis involves the lyophilization of a solution of polylactic acid having a molecular weight of at least 100,000, weight average, at a concentration of at least 3½% by weight of the solution of the polylactic acid. A variety of physiologically acceptable wetting agents is useful, a preferred class being the alkali metal soaps of fatty acids or of alkyl aryl sulfonic acids.

22 Claims, No Drawings

ASSIMILABLE HYDROPHILIC PROSTHESIS

FIELD OF THE INVENTION

This invention relates to an assimilable, porous, hydrophilic prosthesis, and to a process for making it. More particulary, the invention relates to an assimilable, hydrophilic bandange for a dry socket in dental therapy, and a process for making it.

BACKGROUND OF THE INVENTION

For many years those scientists working in support of the medical and dental professions have sought readily assimilable organic polymers that would be useful as surgical repair materials. One application for such materials is in dry socket therapy. After the removal of a third molar, the cavity that is left in the mouth by the extraction of the third molar heals slowly. If an assimilable prosthesis were available, it could be useful for insertion in the socket, to help the healing process.

Polylactic acid has been suggested for use in the past as a surgical repair material. Kulkarni et al., Arch. Surg., Vol. 93, November, 1966, pages 839-843. Polylactic Acid for Surgical Implants. Kulkarni et al., J. Biomed, Mater. Res., Vol. 5, pp. 169-181 (1971), Biodegradable Poly (lactic Acid) Polymers. The use of polyglycolic acid has also been suggested, U.S. Pat. No. 3,463,158. Filaments made from polylactic acid and related materials are suggested in Japanese published patent application No. 2743 (Showa 41-2734), 1966, and U.S. Pat. No. 3,531,561. The hydroxy carboxylic acids, and particularly the alpha hydroxy carboxylic acids, are of particular interest as biodegradable polymers because they may undergo hydrolytic scission to form metabolites normal to the body.

Unfortunately, these polymers, while biodegradable and assimilable, are naturally hydrophobic. Accordingly, when an attempt is made to use a porous shaped body of polylactic acid, for example, in dry socket therapy, blood does not wet the implant, and consequently a clot forms that surrounds the implant and granulation is hindered and retarded rather than helped.

SUMMARY OF THE INVENTION

I have now discovered a biodegradable, assimilable prosthesis that is formed from a porous, hydrophilic polymeric article. This article is formed by the removal of solvent, without substantial dimensional change, from a solution of (a), a biodegradable, assimilable polymer composed primarily of polymerized units of a hydroxy, and preferably an alpha hydroxy, carboxylic acid, preferably those having one to four carbon atoms and (b), a small amount of a physiologically acceptable wetting agent that is sufficient to impart hydrophilicity to the article. When such an article is implanted in a dry socket, it is readily wet by the blood, and eventual granulation is facilitated, so that healing is promoted.

A preferred prosthesis comprises a porous hydrophilic body formed by the lyophilization of a solution of at least 3½% by weight concentration of a polylactic acid, which solution contains a physiologically acceptable wetting agent in a small amount based on the weight of the polymer, which amount is effective to impart hydrophilicity to the body.

DETAILED DESCRIPTION OF THE INVENTION

Biodegradable, assimilable, porous, hydrophilic polymeric bodies can be produced in accordance with the invention in a variety of ways, from a variety of polymers. However, and particularly for use in dry socket therapy, the preferred prosthesis comprises a porous hydrophilic body formed by the freezing and subsequent removal of solvent by sublimation under vacuum (lyophilization) of a solution of at least 3½% and preferably 5% by weight concentration of a polylactic acid, which solution contains a physiologically acceptable wetting agent in a small amount based on the weight of the polymer, which amount is effective to impart hydrophilicity to the porous body. One preferred kind of wetting agent is an alkali metal soap of a fatty acid. Generally the concentration of the wetting agent is at least 1% by weight based on the weight of the polymer, although higher or lower concentrations may be employed.

The molecular weight of the polylactic acid should be at least 100,000, weight average. To prepare a polylactic acid having the molecular weight, the initial ingredients should be exceptionally pure, and the smallest feasible amount of catalyst should be employed.

The initial material employed, to make a polylactic acid, includes the racemic mixture of the optical isomers of lactic acid, or either of the optical isomers, that is, either D(−) or L(+) lactic acid. Alternatively, a lactide may be used as the initial material. The lactide is prepared by distilling water from lactic acid at 140° C. for 8 to 10 hours in the presence of about 2% of zinc oxide, under vacuum at about 100 mm. of mercury. The lactide product is distilled at 2 mm. pressure at about 200° C. to 225° C. The yield of crude lactide product is approximately 95%, and it is then recrystallized, preferably several times, from each of acetone and then from benzene. Alternatively, commercially pure lactide may be employed. While acetone and benezene have been mentioned as solvents from which recrystallization can be accomplished, other solvents, such as ethyl acetate and methyl ethyl ketone, may also be employed.

To convert a lactide to a polylactic acid, the lactide is placed in a polymerization tube or other suitable reaction vessel. Air and any residual solvents are removed by gradually applying vacuum and heat, until the lactide melts. The evacuated reaction vessel is then heated at about 170° C. for 6 to 8 hours, at which time polymer formation is complete. Suitable polymerization catalysts include tin chloride, zinc chloride, lead oxide, tin oxide, zinc oxide, and tetraphenyl tin. The amount of catalyst employed generally is in the range from about 0.001% to 0.01% based on the lactide. For ease in handling, tetraphenyl tin is preferred, particularly for large scale preparations.

The preferred polymer, polylactic acid, is a polymer formed of repeating units of the formula:

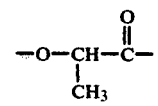

The hydroxy-substituted lower carboxylic acids are preferred to make the polymers that are suitable for use in accordance with the invention. These acids include glycolic acid, beta hydroxy propionic acid, and alpha and beta hydroxy butyric acids. While polylactic acid is the preferred polymer, suitable polymers include those in which the repeating unit has either two or three backbone carbons, according to the formula:

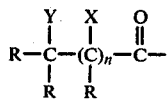

where:

n is 0 or 1;

one of —X and —Y is oxygen, ie, —O—, for connection to another repeating unit, and the other, if present, is R;

R is hydrogen or alkyl up to 18 carbon atoms; and preferably, but not necessarily, the total number of carbon atoms in the "R" substituents does not exceed 18.

Generally, the available alpha hydroxy carboxylic acids are preferred for making satisfactory polymers. Comonomers may be included. For example, when making a polylactic acid from lactide, other materials that may be present in a minor proportion include: glycolide, B-propiolactone, tetramethylglycolide, B-butyrolactone, gamma-butyrolactone, pivalolactone, and intermolecular cyclic esters of alpha hydroxybutyric acid, alpha hydroxyisobutyric acid, alpha hydroxyvaleric acid, alpha hydroxyisovaleric acid, alpha hydroxycaproic acid, alpha hydroxy-alpha-ethylbutyric acid, alpha hydroxyisocaproic acid, alpha hydroxy-B-methylvaleric acid, alpha hydroxyheptanoic acid, alpha hydroxyoctanoic acid, alpha hydroxydecanoic acid, alpha hydroxymyristic acid, alpha hydroxystearic acid, alpha hydroxylignoceric acid, and B-phenyllactic acid.

When a suitable biodegradable, assimilable polymer has been selected, the polymer is placed in solution. A physiologically acceptable wetting agent is then selected, and it is also placed in solution. An appropriate amount of the wetting agent solution is then added to the solution of the polymer. Often different solvents are required for the polymer and for the wetting agent, and they should be selected for compatibility.

Any one of several available techniques can then be employed to remove the solvent or solvents from the solution, without substantial dimensional change, to produce the desired porous body. The preferred technique involves freezing the solution in dry ice, then subjecting the frozen mass to high vacuum, such as a vacuum of about 100 micrometers of mercury, for a sufficient period of time to remove essentially all of the solvent. This may require several hours, and a convenient period is about 24 hours. While lyophilization is the preferred technique for rapid solvent removal without substantial dimensional change, extraction and partition by the use of another solvent are also acceptable techniques.

Since there is little or substantially no dimensional change during solvent removal, the volume of the final body is approximately equal to the original volume of the solution. Thus, if the lyophilized solution contains 5% by weight of polylactic acid, the porous hydrophilic body obtained by lyophilization will be about 95% porous. When a shaped piece made from such a body is inserted in a dry socket, it is readily wet by the blood, and granulation and overall healing are promoted. The wettability of the product is demonstrated by placing a piece of it in a pool of blood; it rapidly wets and sinks in the blood.

The invention may be further exemplified by the specific demonstration thereof that appears in the following example. In this application, all parts and percentages are by weight unless otherwise specified, and all temperatures are on the Celsius scale unless otherwise specified.

EXAMPLE 1

Effect of A Wetting Agent

Commercially available racemic lactide was recrystallized twice from ethyl acetate to insure purity.

A quantity of the purified lactide crystals was placed in a polymerization tube together with 0.02% by weight of the lactide, of tetraphenyl tin. The tube was repeatedly evacuated and flushed with nitrogen, to insure removal of all oxygen from the tube. The tube was then placed under high vacuum and sealed. Polymerization was carried out at 170° C. for 4 hours. The tube was then cooled.

The polymeric product was removed from the tube and dissolved in dioxane in an approximately 20% by weight solution. The polymer was then precipitated from the solution by adding distilled water to the solution. The sticky polymeric product that precipitated was then repeatedly washed with water to remove residual solvent. Finally, the polymeric product was cut into small pieces and dried for 24 hours in air, then under high vacuum. The product was pale yellow in color, very tough, and very hard.

A 1.5% solution of a portion of the polylactic acid was prepared in benzene. Next, a 5% solution was prepared of sodium oleate in a solvent system formed from a mixture of 30% methanol and 70% benzene, by volume. A small amount of the soap solution was then added to the polylactic acid solution, and this was repeated with several different aliquots of the polylactic acid solution, to incorporate, in the polylactic acid solution samples, different amounts of from 0.25% to 2.5% of the sodium oleate based on the weight of the polymer. The several mixtures of the polymer and sodium oleate solutions were then warmed and stirred for about an hour, to insure thorough mixing. They were then frozen in dry ice, then subjected to a high vacuum of about 100 micrometers of mercury for 18 hours.

One example of lyophilized product, containing 2.0% sodium oleate based on the weight of the polymer, was tested and was found to absorb blood immediately when placed in a blood sample. All of the products thus produced were hydrophilic. All appeared to be suitable for use in making dry socket bandages.

Because of the very high porosity and consequent fragility of the porous bodies produced when the polylactic acid concentration is only 1.5% by weight of the solution, it is preferred that the concentration of polymer in the solution to be lyophilized be at least 3.5%. Generally, a 5% concentration can be relied upon to give satisfactory products from the standpoint of porosity coupled with reasonable strength.

While not wishing to be bound by any theory, it is believed that the oleate molecules become come to the surface of the polymer, and are oriented, to impart hydrophilicity to the polymer.

EXAMPLE 2

Use of Other Wetting Agents

A stock solution was prepared by dissolving 15 grams of polylactic acid in 1,000 milliliters of benzene. In each of the following demonstrations of the invention, 50 milliliters of the polylactic acid solution were employed, containing 0.75 grams of polylactic acid. In each of these demonstrations, the solution of wetting agent was prepared at 5% concentration of the wetting agent in a liquid vehicle made up of 30% methanol and 70% benzene, by volume.

To form the mixed solution of polylactic acid and wetting agent, 50 milliliters of the polylactic acid solution was warmed and shaken with the respective indicated amount of the solution of the wetting agent. Agitation and warming was continued for about 1 hour, until the mixed solution became homogeneous. The solution was then placed in the lyophilizing flask and frozen in a dry ice-acetone mixture, until it became thick and semi-solid. At that time, the lyophilizing flask was connected to the manifold of the lyophilizer. The rapid application of high vacuum insured the production of a highly porous body having an interconnected pore structure, and hydrophilic to the extent indicated by the results.

| Run No. | Wetting Agent | Millimeters of Wetting Agent Solution Added to the Polylactic Acid Solution | % by Weight of Wetting Agent Based on Polymer |
|---|---|---|---|
| 2-1 | Brij[1] | 0.75 | 5 |
| 2-2 | Brij | 1.125 | 7.5 |
| 2-3 | Tween[2] 80 | 0.75 | 5 |
| 2-4 | Tween 80 | 1.125 | 7.5 |
| 2-5 | Ultrawet[3] 60L | 0.75* | 5.0 |
| 2-6 | Ultrawet 60L | 1.125* | 7.5 |

[1]Brij is a trademark of Atlas Powder Co. for a polyoxyethylene derivative of lauryl alcohol.
[2]Tween is a trademark of Atlas Powder Co. for nonionic surface-active agents that are polyoxyalkylene derivatives of hexitol anhydride partial long chain fatty acid esters. Tween 80 is reported to be sorbitan monooleate.
[3]Ultrawet is a trademark of Atlantic Refining Co. for a line of alkyl aryl sulfonate-type, anionic surface active agents. Ultrawet 60L is a clear, pale yellow liquid.
*The liquid vehicle for the solution of Ultraweb wetting agent was 50% methanol mixed with 50% benzene, by volume.

The lyophilized products obtained were fluffy, porous solids. Similar specimens of each product were placed in the pool of blood, and the time required for absorption of blood by the sample was noted.

| Sample No. | Time Required for Absorption of Blood |
|---|---|
| 2-1 | 3 hours |
| 2-2 | 2 hours |
| 2-3 | 4 hours |
| 2-4 | 4 hours |
| 2-5 | 45 seconds |
| 2-6 | 1 minute |

While all these specimens indicated that the character of the polylactic acid had been converted from hydrophobic to hydrophilic clearly the Ultrawet wetting agent produced the most rapid wetting, which indicates characteristics most favorable for dry socket bandaging. Comparable results as to absorption time are obtained when the concentration of polylactic acid is 3.5%, 5%, or higher, but the bandage is stronger. Comparable results are also obtained whether the physiologically acceptable wetting agent is nonionic, anionic, or cationic.

General

Despite the fact that the examples report successful demonstrations of the invention at relatively low polymer concentrations, it has been found that polymer concentrations of at least 3.5% by weight, in the polymer solutions, are preferable. These higher concentrations lead to much more substantial porous structures with respect to strength, maintenance of integrity, ease of handling, and the like.

Similar results are obtained when the demonstrations of the invention are repeated using as the polymer not only polylactic acid, but also poly (beta-hydroxy propionic acid), and mixed polymers formed by producing co-polymers having repeating units that are primarily derived from lactic acid, glycolic acid, beta-hydroxy propionic acid, and alpha-hydroxy butyric acid.

Similarly, in place of the wetting agents whose use is described in the foregoing demonstrations of the invention, it is feasible to use other alkali metal soaps of fatty acids, alkyl aryl sulphonates and the like. While not wishing to be bound by any theory, it appears that the interfacial tension between the surfaces of polylactic acid, or other poly (alpha or beta hydroxy carboxylic acid), and water or the body fluids such as blood, is usually high. The surface of the polymer requires conditioning in order to reduce the interfacial tension, to the point where a liquid in contact with it will spread over the surface. For this purpose, according to the present invention, either natural or synthetic physiologically acceptable surface active agents, wetting agents, or detergents are used, generally to the extent of 0.1% to 5% based on the weight of the polymer. These are all referred to herein as "wetting agents." When properly prepared for use as a dry socket bandage in accordance with this invention, the wetting agent appears to be adsorbed in the polymer, possibly molecularly adsorbed.

The selected wetting agent is generally used by dissolving it in benzene and/or dioxane, along with the polymer, with warming and agitation to insure a homogeneous distribution, generally for an hour or so. Thereafter the solvent is removed by lyophilization or by extraction with another selective solvent that does not dissolve the polymer and the wetting agent, to form the porous, hydrophilic polymeric article.

Suitable wetting agents include alkali metal, amine, and ammonium salts of natural and synthetic fatty acids, sulfonated and sulfated fatty alcohols, polyphosphoric acids, alkyl aryl sulfonic acids, and the like. Generally the wetting agent may be nonionic, cationic, or anionic.

The important criteria are that it be physiologically acceptable and capable of rendering the polymer hydrophilic. Among the preferred wetting agents are the following: Ultrawet 60L; Aerosol OT (a trademark of American Cyanamid Co.); octadecyl ammonium chloride; Tween 80; sorbitol oleate; and sodium oleate.

While lyophilization is a preferred production technique for making a porous body in accordance with the present invention, other techniques can be employed including, for example, extraction, or partition by another solvent. For example, the suitable polymer, preferably polylactic acid, is dissolved in dioxane. To this is added a sufficient quantity of a dilute solution of sodium oleate to bring the amount of sodium oleate added to the level of about 1.5% based on the polylactic acid present. After warming and stirring for about an hour, to insure homogeneity, a sufficient quantity of ordinary table salt (sodium chloride) is added to produce a solution at a concentration of about 30% by weight of the salt. The thick mass that results is then quickly immersed in water. Since both dioxane and salt are readily soluble in water, the water extracts both the dioxane and the salt over a period of time with slow agitation. As before, the porosity of the finished body depends upon, among other things, the amount of salt and the amount dioxane or other solvent solvent removed by extraction with water. At least 90% porosity is preferred. There is relatively little dimensional change, whether the material is lyophilized or extracted in the manner just described.

Products prepared in accordance with the present invention should be sterile at the time of use. Sterilization preferably is accomplished by irradiation with gamma-rays, at an exposure dose of 2 megarads, and this may be done before or after enclosing a suitable-sized piece of the product within a plastic protective envelope, that will maintain microbiological integrity until the package is broken into for use.

While the invention has been disclosed herein by reference to the details of several specific embodiments thereof, it is to be understood that the disclosure is intended in an illustrative rather than in a limiting sense, and it is contemplated that various modifications in the compositions and in the processes of making the finished articles will readily occur to those skilled in the art, that are within the spirit of the invention and within the scope of the appended claims.

I claim:

1. An assimilable prosthesis than can be implanted in a body cavity, comprising a porous hydrophilic body formed by the removal of solvent by lyophilization or selective leaching, without substantial volume change, from a substantially homogeneous solution in liquid organic solvent of (a), an assimilable normally hydrophobic polymer composed primarily of polymerized units of a saturated, aliphatic hydroxy carboxylic acid, and (b), a small amount of a physiologically acceptable wetting agent, which amount remains in the polymer and is sufficient to impart hydrophilicity to said body.

2. A prosthesis in accordance with claim 1 that is formed from a solution containing at least 3.5% by weight of the assimilable polymer.

3. A prosthesis in accordance with claim 1 wherein the polymer is a lactic acid polymer having a molecular weight of at least 100,000, weight average.

4. A prosthesis in accordance with claim 1 wherein the carboxylic acid polymer is polylactic acid having a molecular weight of at least 100,000, weight average.

5. A prosthesis in accordance with claim 1 wherein the carboxylic acid contains not more than four carbon atoms and the polymer has a molecular weight of at least 100,000, weight average.

6. An assimilable prosthesis in accordance with claim 1 comprising a porous hydrophilic body formed of a polymer of repeating units of the formula:

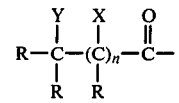

where: n is 0 or 1; one of -X and -Y is oxygen, ie, —O—, for connection to another repeating unit, and the other, if present, is R; and R is H or alkyl up to 18 carbon atoms.

7. A prosthesis in accordance with claim 6 wherein the total number of carbons in the R substituents is 18.

8. A prosthesis in accordance with claim 6 wherein the wetting agent is a nonionic, cationic, or anionic synthetic wetting agent.

9. An assimilable prosthesis in accordance with claim 1 comprising a hydrophilic body that is at least 90% porous and that is formed from an assimilable polymer of an alpha or beta hydroxy carboxylic acid having not more than four carbon atoms, the molecular weight of the polymer being at least 100,000, weight average, and said polymer having intimately distributed therein the small amount of physiologically acceptable wetting agent.

10. A prosthesis in accordance with claim 9 wherein the concentration of the polymer in the solution is at least 3.5% by weight.

11. An assimilable prosthesis in accordance with claim 9, for insertion in a dry socket to facilitate healing, comprising a hydrophilic body formed by the lyophilization of a solution of at least 3.5% by weight concentration of a polylactic acid that has a molecular weight of at least 100,000, weight average, which solution contains a physiologically acceptable wetting agent in a small amount up to 5% based on the weight of the polymer, which amount is effective to impart hydrophilicity of the body.

12. A prosthesis in accordance with claim 11 wherein the wetting agent is an alkali metal soap of a fatty acid having from 8 to 18 carbon atoms, inclusive.

13. A prosthesis in accordance with claim 12 wherein the soap is sodium oleate.

14. A process for making an assimilable, porous, hydrophilic article that can be implanted in a body cavity, comprising preparing a substantially homogeneous solution in a liquid organic solvent of a normally hydrophilic polymer formed of repeating units of the formula:

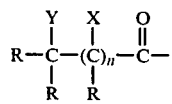

where, n is 0 or 1; one of —X and —Y is oxygen, ie, —O—, for connection to another repeating unit, and the other, if present, is R; and R is H or alkyl up to 18 carbon atoms; said solution containing a small amount, homogeneously distributed therein, and sufficient to impart hydrophilicity to the article, of a physiologically acceptable wetting agent, and then removing the solvent from the solution by lyophilization or selective leaching, without substantial change in volume, to produce the desired porous article, the wetting agent remaining in the polymer and imparting hydrophilicity to the article.

15. A process in accordance with claim 14 wherein the concentration of polymer in the solution is at least 3.5% by weight.

16. A process for making an assimilable, porous, hydrophilic article that can be implanted in a body cavity, comprising admixing a solution of a normally hydrophobic polymer of an aliphatic, saturated, alpha or beta hydroxy carboxylic acid having up to four carbon atoms with a small amount of a physiologically acceptable wetting agent, and removing the solvent from the solution without substantial volume change thereof, by lyophilization or selective leaching, to produce the desired porous article, the wetting agent remaining in the polymer and imparting hydrophilicity to the article.

17. A process in accordance with claim 16 wherein the concentration of the polymer in the solution is at least 3.5% by weight.

18. A process in accordance with claim 17 wherein the polymer is a lactic acid polymer having a molecular weight of at least 100,000.

19. A process for making an assimilable, porous, hydrophilic article that can be implanted in a body cavity, comprising admixing a solution of normally hydrophobic polymer of lactic acid having a molecular weight of at least 100,000, weight averge, with a small amount of a physiologically acceptable wetting agent, and freeze-drying the admixture to obtain the desired porous article, the wetting agent remaining in the polymer and imparting hydrophilicity to the article.

20. A process in accordance with claim 19 wherein the concentration of the polymer in the solution is at least 3.5% by weight.

21. A process in accordance with claim 19 wherein the wetting agent is a synthetic wetting agent.

22. A process in accordance with claim 19 wherein the wetting agent is the salt of an alkali metal with a fatty acid having 8 to 18 carbon atoms.

* * * * *